US012782174B2

(12) United States Patent
Suwito et al.

(10) Patent No.: US 12,782,174 B2
(45) Date of Patent: Nov. 3, 2026

(54) METHOD FOR CALCULATING INFUSION RATE USING A DRIP CHAMBER

(71) Applicant: CareFusion 303, Inc., San Diego, CA (US)

(72) Inventors: Wantjinarjo Suwito, West Linn, OR (US); Ryan Callahan, Long Beach, CA (US)

(73) Assignee: CAREFUSION 303, INC., San Diego, CA (US)

( * ) Notice: Subject to any disclaimer, the term of this patent is extended or adjusted under 35 U.S.C. 154(b) by 281 days.

(21) Appl. No.: 18/608,340

(22) Filed: Mar. 18, 2024

(65) Prior Publication Data

US 2024/0361161 A1 Oct. 31, 2024

Related U.S. Application Data

(60) Provisional application No. 63/462,900, filed on Apr. 28, 2023.

(51) Int. Cl.
*A61M 5/168* (2006.01)
*G01F 1/00* (2022.01)

(52) U.S. Cl.
CPC ......... *G01F 1/007* (2013.01); *A61M 5/16804* (2013.01)

(58) Field of Classification Search
CPC .... A61M 5/168–16827; A61M 5/16877–1689
See application file for complete search history.

(56) References Cited

U.S. PATENT DOCUMENTS

| | | | | | |
|---|---|---|---|---|---|
| 3,625,211 | A | * | 12/1971 | Butler | A61M 5/1412 604/257 |
| 3,664,339 | A | | 5/1972 | Santomieri | |
| 4,106,675 | A | | 8/1978 | Taylor | |
| 4,432,761 | A | * | 2/1984 | Dawe | A61M 5/1689 250/559.21 |
| 5,588,963 | A | * | 12/1996 | Roelofs | G01F 3/00 604/65 |

(Continued)

FOREIGN PATENT DOCUMENTS

GB 858731 A 1/1961

OTHER PUBLICATIONS

Mometrix, “Calculating IV Drip Rates”, Mometrix Test Preparation, last updated Aug. 30, 2024, retrieved from the internet at: https://www.mometrix.com/academy/calculations-of-drip-rates/.

(Continued)

*Primary Examiner* — Alexander A Mercado
(74) *Attorney, Agent, or Firm* — MASCHOFF BRENNAN

(57) ABSTRACT

A method for calculating an infusion rate in a drip chamber includes: providing a housing that receives a fluid, the housing received the fluid at a distal end and expels the fluid at a proximal end, the housing includes a reference mark; receiving, at the proximal end of the housing, a flow controller rotatably coupled to the housing, the flow controller includes an aperture extending therethrough; rotating the flow controller relative to the housing such that the aperture prevents the fluid from traveling therethrough; and determining the infusion rate by measuring a time elapsed until the fluid reaches the reference mark in the housing.

20 Claims, 5 Drawing Sheets

(56) References Cited

U.S. PATENT DOCUMENTS

| | | | | |
|---|---|---|---|---|
| 2010/0309005 | A1* | 12/2010 | Warner | G01F 15/06 702/46 |
| 2012/0186509 | A1* | 7/2012 | Milijasevic | A61M 5/16854 116/266 |
| 2013/0085443 | A1* | 4/2013 | Lowery | G01F 1/72 604/65 |
| 2014/0283620 | A1* | 9/2014 | Kolko | G16H 20/17 73/861.41 |
| 2016/0073063 | A1* | 3/2016 | Peret | A61M 5/16877 348/160 |
| 2017/0216521 | A1* | 8/2017 | Kolko | G01F 3/00 |
| 2018/0193559 | A1* | 7/2018 | Hirata | G01F 1/72 |
| 2019/0247575 | A1* | 8/2019 | Kolko | A61M 5/1414 |
| 2020/0114073 | A1* | 4/2020 | Kolko | G01F 1/704 |
| 2022/0133995 | A1* | 5/2022 | Lekkala | A61M 5/1411 604/246 |
| 2022/0395635 | A1 | 12/2022 | Malloy | |
| 2023/0398293 | A1* | 12/2023 | Yoo | A61M 5/1411 |

OTHER PUBLICATIONS

International Search Report and Written Opinion for Application No. PCT/US2024/025681, dated Aug. 14, 2024, 13 pages.

* cited by examiner

Closed

Open

METHOD FOR CALCULATING INFUSION RATE USING A DRIP CHAMBER

CROSS REFERENCE TO RELATED APPLICATION

This application claims the benefit of priority under 35 U.S.C. § 119 to U.S. Provisional Patent Application Ser. No. 63/462,900, entitled "METHOD FOR CALCULATING INFUSION RATE USING A DRIP CHAMBER", filed on Apr. 28, 2023, the entire contents of which is incorporated herein by reference.

FIELD OF THE INVENTION

The present disclosure generally relates to drip chambers, and, in particular, to a method for calculating infusion rate using a drip chamber.

BACKGROUND

Medical treatments often include the infusion of a medical fluid (e.g., a saline solution or a liquid medication) to patients using an intravenous (IV) set which generally includes a connector for connection to a fluid reservoir or IV bag, a drip chamber used to determine the infusion rate of fluid from the fluid reservoir, an intravenous fluid line for providing a connection between the fluid reservoir and the patient, and a catheter that may be positioned intravenously in a patient.

The drip chamber is generally designed to encourage liquid entering the drip chamber to form droplets that fall toward the bottom of the chamber. By forming droplets, an attendant is able to determine the flow rate of liquid through the IV set by counting the number of droplets that fall over a period of time. However, if the height of the liquid exceeds the operable liquid height of the drip chamber, the flow rate of liquid through the IV set may be difficult or impossible to determine. To facilitate the counting of droplets and to permit the drip chamber to fill with liquid to an operable liquid height, the drip chamber is typically made of a clear flexible plastic. However, the fluid drop size can vary depending on the size of the aperture through which the fluid enters the drip chamber. Thus, determining the type of drip chamber (macro or micro drip) is a pre-requisite.

Accordingly, a need exists for an IV set that allows for an accurate calculation of infusion rate within the drip chamber regardless of the drip size.

SUMMARY

In one embodiment there is a method for calculating an infusion rate in a drip chamber, the method including providing a housing receiving a fluid, the housing configured to receive the fluid at a distal end and expel the fluid at a proximal end, the housing including a reference mark, receiving, at the proximal end of the housing, a flow controller rotatably coupled to the housing, the flow controller including an aperture extending therethrough, rotating the flow controller relative to the housing such that the aperture prevents the fluid from traveling therethrough, and determining the infusion rate by measuring a time elapsed until the fluid reaches the reference mark in the housing.

In some embodiments, the flow controller includes an inner member and an outer member, the inner member being fixed relative to the housing and the outer member being rotatable relative to the inner member. In some embodiments, the outer member and the inner member each include an aperture extending therethrough. In some embodiments, rotating the outer member relative to the inner member such that the apertures do not align prevents the fluid from traveling through the flow controller.

In some embodiments, a volume of the housing at the reference mark is known. In some embodiments, determining the infusion rate includes dividing the volume by the time elapsed until the fluid reaches the reference mark. In some embodiments, the housing includes more than one reference mark. In some embodiments, the method further includes receiving, at a proximal end of the flow controller, a tubing configured to receive the fluid. In some embodiments, the flow controller includes more than one aperture.

In one embodiment, there is a method for calculating an infusion rate in a drip chamber, the method including providing a housing receiving a fluid, the housing configured to receive the fluid at a distal end and expel the fluid at a proximal end, receiving, in the housing, a flow collector and determining the infusion rate by measuring a time elapsed until the fluid fills the flow collector.

In some embodiments, the flow collector includes a septum at a proximal end thereof. In some embodiments, a radial force acting upon the flow collector opens the septum thereby establishing a fluid pathway therethrough. In some embodiments, a volume of the flow collector is known. In some embodiments, determining the infusion rate includes dividing the volume by the time elapsed until the fluid fills the flow collector. In some embodiments, the flow collector has a diameter smaller than a diameter of the housing.

In some embodiments, the method further includes receiving, at a proximal end of the housing, a tubing configured to receive the fluid. In some embodiments, the flow collector is coupled to the housing by at least one arm. In some embodiments, the flow collector is received at a center of the housing. In some embodiments, the flow collector is fixed relative to the housing. In some embodiments, the flow collector allows for continuous use of the drip chamber when filled with the fluid.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, such embodiments can be used in other fluid conveyance systems. Furthermore, various applications of such embodiments and modifications thereto, which may occur to those who are skilled in the art, are also encompassed by the general concepts described herein.

In accordance with some embodiments, the present disclosure includes various features and advantages of a fluid connector assembly with medical connectors that seal off their respective fluid paths when the medical connectors are decoupled from each other. The medical connectors may each include a compressible member that decompresses in response to the decoupling, thus providing an automatic sealing of the respective fluid paths.

Figure 1:
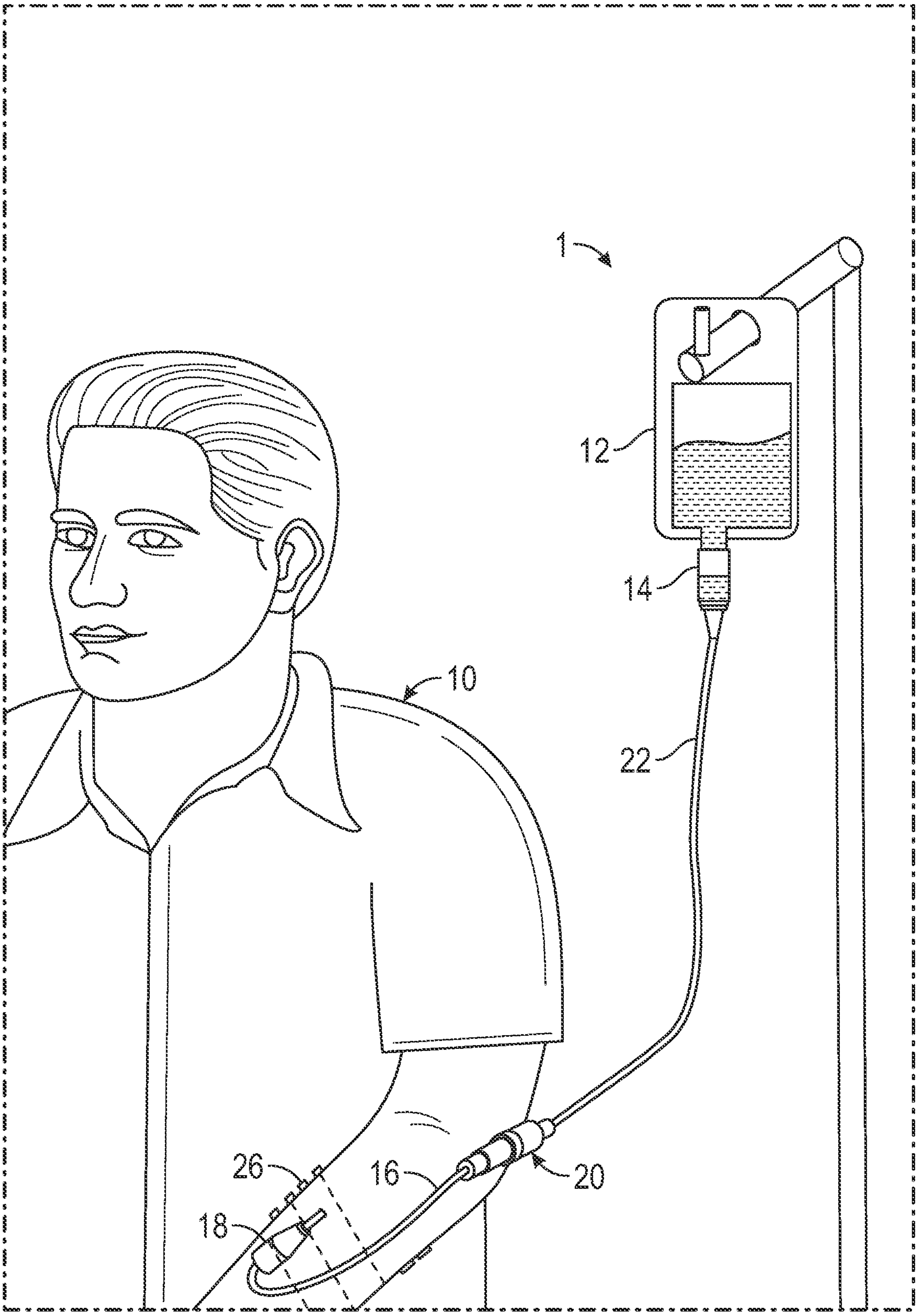
FIG. 1 illustrates an IV set coupled to a patient, in accordance with aspects of the present disclosure.

Referring now to the figures, FIG. 1 illustrates an IV set 1 coupled to a patient 10, in accordance with aspects of the present disclosure. The IV set 1 may include a medicament bag 12, a drip chamber 14, and tubing 22. The tubing 22 may extend between the drip chamber 14 and a fluid connector 20 of the IV set 1. To resist unintended dislodgement or disconnection of the tubing 16 or the catheter 18 from the patient, tape 26 is placed over the tubing 16 and the catheter 18, so that the tape 26 engages the tubing 16, the catheter 18, and the patient 10.

Figure 2:
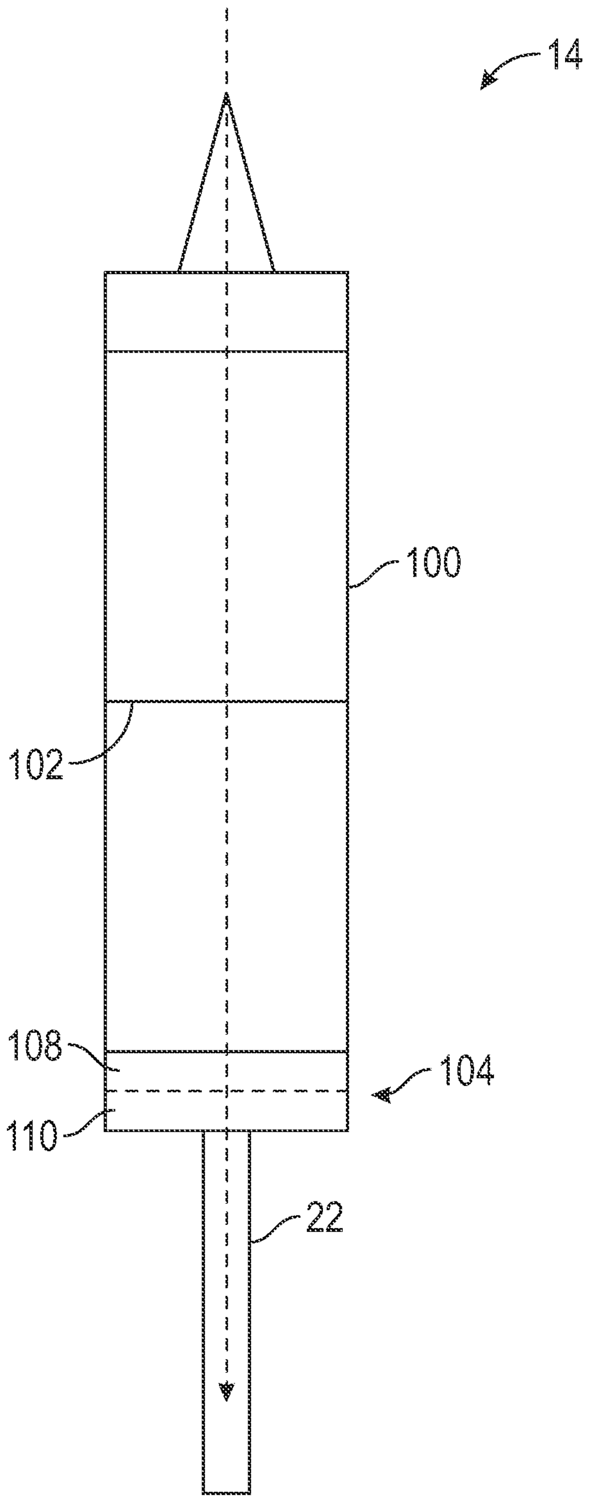
FIG. 2 illustrates a drip chamber of the IV set of FIG. 1 according to an exemplary embodiment.

FIG. 2 illustrates the drip chamber 14 including a housing 100 having a proximal end and a distal end. In one embodiment, a method for calculating an infusion rate of the fluid in the drip chamber 14 may include providing the housing 100. The housing 100 may receive the fluid at the distal end and expel the fluid at the proximal end, as shown by the broken line in FIG. 2. The drip chamber 14 may be configured such that the fluid received through the distal end travels toward the proximal end without contacting the housing 100. The drip chamber 14 may receive the fluid from, for example, a medicament bag 12 or other source. The housing 100 may have a generally cylindrical cross-section. In one embodiment, the housing 100 has a generally polygonal cross-section. The housing 100 may comprise a glass or plastic material. The housing 100 may be transparent to allow viewing of the fluid. In one embodiment, the housing 100 may be made of a deformable material to allow the housing 100 to deform in response to an axial force acting thereon. The fluid may be a solution such as glucose, saline solution, medical dyes, and medicament in liquid form. The distal end of the housing 100 may be located above the proximal end in the IV set 1.

The housing 100 may include one or more graphics, such as a logo or other indicia. The housing 100 may include a reference mark 102 indicating a fluid volume between the proximal end of the housing 100 and the reference mark 102. The volume at the housing 100 at the reference mark 102 may be known. In one embodiment, the reference mark 102 may indicate a fluid volume between the distal end of the housing 100 and the reference mark 102. In one embodiment, the housing 100 includes more than one reference mark 102. The reference mark 102 may extend around the housing 100 such that it can be viewed from all sides. In one embodiment, the reference mark 102 extends around a portion of the housing. The reference mark 102 may include any combination of letters and shapes. The reference mark 102 may be engraved in the housing 100, or may be coupled to a surface of the housing 100 by an adhesive.

In some embodiments, the method may further include receiving a flow controller 104 at the proximal end of the housing 100. The flow controller 104 may be a generally cylindrical member with a diameter similar to that of the housing 100. In one embodiment, the flow controller is polygonal shaped. The flow controller 104 may have a diameter larger than the housing 100. The flow controller 104 may have a diameter smaller than the housing 100. The flow controller 104 may be rotatably coupled to the housing 100 and may comprise an aperture 106 extending therethrough. In one embodiment, the flow controller 104 includes more than one aperture extending therethrough. The aperture may be spaced apart from a center 111 of the flow controller 104 . . . . The flow controller 104 may be rotatable between an open position where fluid is permitted to travel through the aperture 106 and a closed position where the fluid is prevented from traveling through the aperture 106. In some embodiments, rotating the flow controller 104 relative to the housing 100 may move the flow controller 104 between the open position and the closed position.

Figure 3:
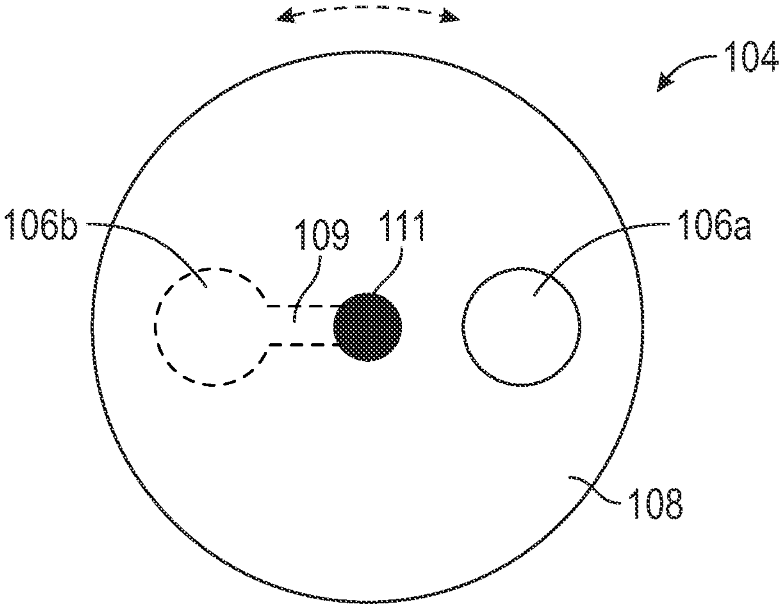
FIG. 3 illustrates a top view of a flow controller of the drip chamber of the IV set of FIG. 1 according to an exemplary embodiment.
Figure 3:
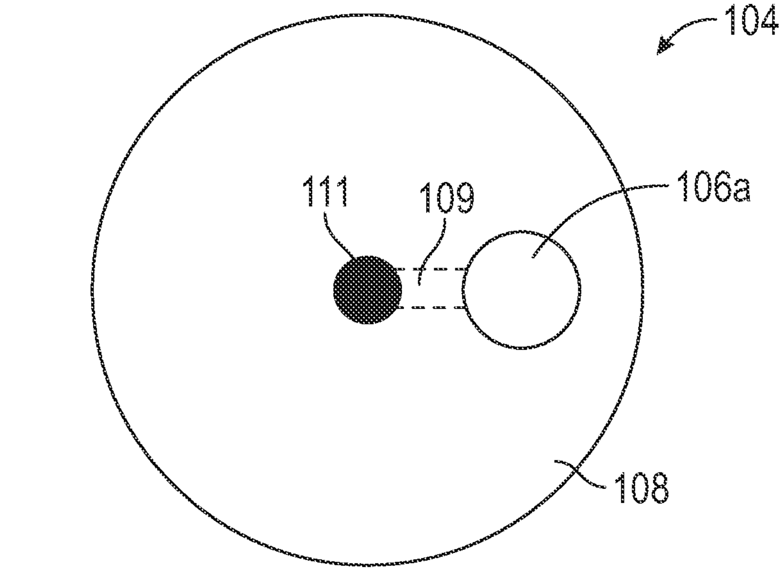

The flow controller 104 may include an inner member 108 and an outer member 110. The inner member 108 may be fixed relative to the housing 100. The outer member 110 may be rotatably coupled to the inner member 108. The outer member 110 may receive the tubing 22. In one embodiment, the outer member 110 is rotatably coupled to the tubing 22. In one embodiment, both the inner member 108 and the outer member 110 are rotatable relative to the housing 100. Referring now to FIG. 3, the inner member 108 and the outer member 110 may include apertures **106*a* and 106*b*, respectively. In one embodiment, apertures 106*a* and 106*b* extend through the inner member 108 and outer member 110, respectively. In one embodiment, aperture 106*b* extends only partially through the outer member 110. Rotation of the outer member 110 relative to the inner member 108 such that aperture 106*a* and aperture 106*b* do not align may prevent the fluid from traveling through the flow controller 104. The outer member 110 may rotate 360 degrees relative to the inner member 108. In one embodiment, the outer member 110 rotates less than 360 degrees relative to the inner member 108. In one embodiment, the outer member 110 is permitted to rotate 180 degrees or 90 degrees relative to the inner member 108. When aperture 106*a* and aperture 106*b* do not align the flow controller 104 may be in the closed position. When aperture 106*a* and aperture 106*b* do align the flow controller 104 may be in the open position. In the open position, the fluid at the proximal end of the housing 100 may be directed through the flow controller 104 to the tubing 22. The inner member 108 may include a channel 109 directing the fluid from the aperture 106 to the tubing 22**.

In one embodiment, the infusion rate of the fluid in the drip chamber 14 may be determined by measuring the time elapsed from the time the flow controller 104 is moved to the closed position until the fluid reaches the reference mark 102 of the housing 100. The measurement of time may include use of a timer, stopwatch, or other appropriate timing method. The infusion rate may be equal to the volume of fluid required to reach the reference mark 102 divided by the time elapsed until the drip chamber 14 fills to the reference mark 102. The infusion rate may be measured in mL/hr. In one embodiment, the infusion rate is measured in one of, for example, L/s, mL/s, L/min, mL/min.

After the flow rate is determined using the above calculation, the flow controller 104 may be rotated to the open position to allow the fluid to travel into the tubing 22. In one embodiment, rotating the flow controller 104 to the open position may empty the drip chamber 14. The flow controller 104 may be rotated to a partial open position by partially aligning aperture **106*a* and aperture 106*b* to modulate the amount of the fluid that is expelled into the tubing 22**.

Figure 4:
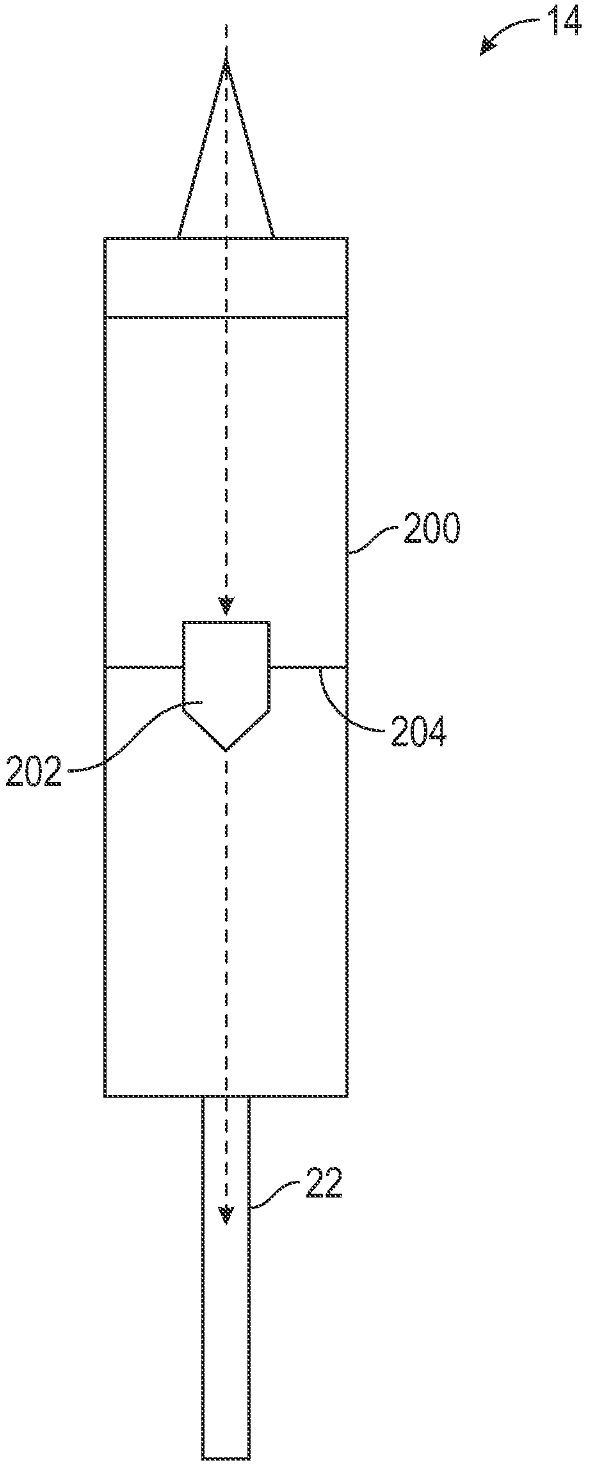
FIG. 4 illustrates a drip chamber of the IV set of FIG. 1 according to an exemplary embodiment.
Figure 5:
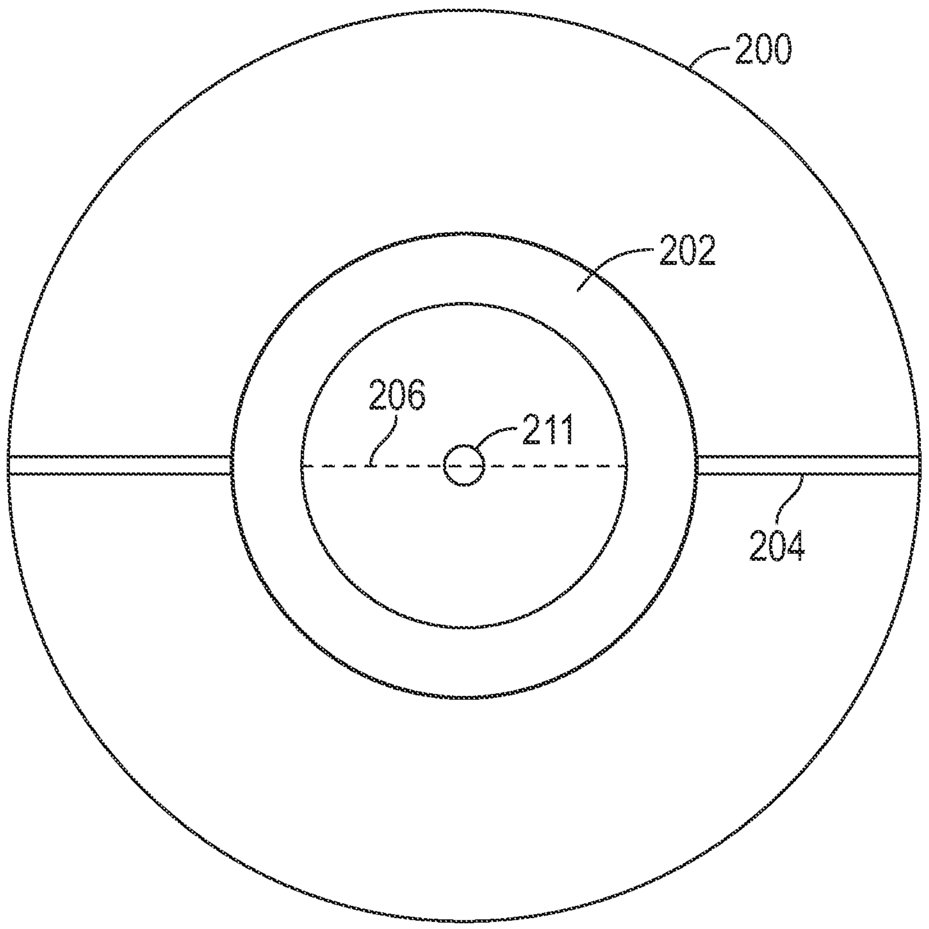
FIG. 5 illustrates a top view of a flow collector of the drip chamber of the IV set of FIG. 1 according to an exemplary embodiment.

FIG. 4 illustrates the drip chamber 14 including a housing 200 having a proximal end and a distal end. In one embodiment, a method for calculating an infusion rate of the fluid in the drip chamber 14 may include providing the housing 200. The housing 200 may receive the fluid at the distal end and expel the fluid at the proximal end, as shown by the broken line in FIG. 4. The drip chamber 14 may be configured such that the fluid received through the distal end travels toward the proximal end without contacting the housing 200. The drip chamber 14 may receive the fluid from, for example, a medicament bag 12 or other source. The housing 200 may have a generally cylindrical cross-section. In one embodiment, the housing 200 has a generally polygonal cross-section. The housing 200 may comprise a glass or plastic material. The housing 200 may be transparent to allow viewing of the fluid. In one embodiment, the housing 200 may be made of a deformable material to allow the housing 200 to deform in response to an axial force acting thereon. The fluid may be a solution such as glucose, saline solution, medical dyes, and medicament in liquid form. The distal end of the housing 200 may be located above the proximal end in the IV set 1.

The drip chamber 14 may include a flow collector 202 disposed in the housing 200. The flow collector 202 may be fixed relative to the housing 200. The flow collector may include a rubber or soft plastic capable of deformation. The flow collector 202 may be received at a central portion between the proximal end and the distal end of the housing 200. In one embodiment, the flow collector 202 is disposed proximate the proximal end or the distal end of the housing 200. The flow collector 202 may be a generally cylindrical shape with a diameter smaller than the housing 200. In one embodiment, the flow collector 202 has a diameter similar to that of the housing 200. The flow collector 202 may be coupled to the housing by an arm 204 extending from the housing 200 to the flow collector 202. In one embodiment, more than one arm extends from the housing 200 to the flow collector 202. The flow collector 202 may include a distal side that is generally open and sized to receive the fluid entering the drip chamber 14.

The flow collector 202 may include a proximal side that is closed. The proximal side of the flow collector 202 may be sloped toward a center 211 having a generally conical shape. The proximal side of the flow collector 202 may include a septum 206 extending therethrough. The septum 206 may extend across the full diameter of the flow collector 202. In some embodiment, the septum 206 extends only partially across the diameter of the flow collector 202. The septum 206 may prevent the fluid from passing therethrough in a closed position and allow the fluid to pass therethrough in an open position. A radial force acting upon the flow collector 202 may open the septum 206 thereby establishing a fluid pathway therethrough. The radial force may cause the arm 204 to reduce the cross sectional diameter of the flow collector 202. The radial force on the flow collector 202 may be generated by the housing 200 deforming inwardly by, for example, a thumb and finger.

In one embodiment, the infusion rate of the fluid in the drip chamber 14 may be determined by measuring the time elapsed until the fluid fills the flow collector 202. The volume of the flow collector 202 may be known. Determining the infusion rate may include dividing the known volume of the flow collector 202 by measured time elapsed until the fluid fills the flow collector 202. The measurement of time may include use of a timer, stopwatch, or other appropriate timing method. The infusion rate may be equal to the volume of fluid required to fill the flow collector 202 divided by the time elapsed until the flow collector 202 fills. The infusion rate may be measured in mL/hr. In one embodiment, the infusion rate is measured in one of, for example, L/s, mL/s, L/min, mL/min.

After the flow rate is determined using the calculation above, a radial force may be exerted on the flow collector 202 to open the septum 206 and empty the flow collector. The flow collector 202 may allow for continuous use of the drip chamber 14 when filled with the fluid. During continuous use, the liquid may overflow over the distal end of the flow collector 202 and be expelled into the tubing 22 from the proximal end of the housing 200.

Illustration of Subject Technology as Clauses

Clause 1. A method for calculating an infusion rate in a drip chamber, the method comprising: providing a housing receiving a fluid, the housing configured to receive the fluid at a distal end and expel the fluid at a proximal end, the housing comprising a reference mark; receiving, at the proximal end of the housing, a flow controller rotatably coupled to the housing, the flow controller comprising an aperture extending therethrough; rotating the flow controller relative to the housing such that the aperture prevents the fluid from traveling therethrough; and determining the infusion rate by measuring a time elapsed until the fluid reaches the reference mark in the housing.

Clause 2. The method of Clause 1, wherein the flow controller comprises an inner member and an outer member, the inner member being fixed relative to the housing and the outer member being rotatable relative to the inner member.

Clause 3. The method of Clause 2, wherein the outer member and the inner member each comprise an aperture extending therethrough.

Clause 4. The method of Clause 3, wherein rotating the outer member relative to the inner member such that the apertures do not align prevents the fluid from traveling through the flow controller.

Clause 5. The method of Clause 1, wherein a volume of the housing at the reference mark is known.

Clause 6. The method of Clause 5, wherein determining the infusion rate comprises: dividing the volume by the time elapsed until the fluid reaches the reference mark.

Clause 7. The method of Clause 1, wherein the housing comprises more than one reference mark.

Clause 8. The method of Clause 1, further comprising: receiving, at a proximal end of the flow controller, a tubing configured to receive the fluid.

Clause 9. The method of Clause 1, wherein the flow controller comprises more than one aperture.

Clause 10. A method for calculating an infusion rate in a drip chamber, the method comprising: providing a housing receiving a fluid, the housing configured to receive the fluid at a distal end and expel the fluid at a proximal end; receiving, in the housing, a flow collector; and determining the infusion rate by measuring a time elapsed until the fluid fills the flow collector.

Clause 11. The method of Clause 10, wherein the flow collector comprises a septum at a proximal end thereof.

Clause 12. The method of Clause 11, wherein a radial force acting upon the flow collector opens the septum thereby establishing a fluid pathway therethrough.

Clause 13. The method of Clause 10, wherein a volume of the flow collector is known.

Clause 14. The method of Clause 13, wherein determining the infusion rate comprises: dividing the volume by the time elapsed until the fluid fills the flow collector.

Clause 15. The method of Clause 10, wherein the flow collector has a diameter smaller than a diameter of the housing.

Clause 16. The method of Clause 10, further comprising: receiving, at a proximal end of the housing, a tubing configured to receive the fluid.

Clause 17. The method of Clause 10, wherein the flow collector is coupled to the housing by at least one arm.

Clause 18. The method of Clause 10, wherein the flow collector is received at a center of the housing.

Clause 19. The method of Clause 10, wherein the flow collector is fixed relative to the housing.

Clause 20. The method of Clause 10, wherein the flow collector allows for continuous use of the drip chamber when filled with the fluid.

Further Considerations

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A method for calculating an infusion rate in a drip chamber, the method comprising:

providing a housing configured to receive the fluid at a distal end and expel the fluid at a proximal end, the housing comprising a reference mark;

receiving, at the proximal end of the housing, a flow controller rotatably coupled to the housing, the flow controller comprising an inner member with a first aperture and an outer member with a second aperture;

rotating the outer member relative to the housing to transition the flow controller from a closed position, in which the first and second apertures prevent the fluid from traveling therethrough, to an open position, in which the fluid is permitted to travel through the first and second apertures; and measuring a time elapsed between transitioning the flow controller from the closed position to the open position and the fluid reaches the reference mark.

2. The method of claim 1, wherein the inner member is fixed relative to the housing and the outer member is rotatable relative to the inner member.

3. The method of claim 1, wherein rotating the outer member relative to the housing to transition the flow controller from the closed position to the open position comprises rotating the outer member relative to the inner member such that the first apertures aligns with the second aperture.

4. The method of claim 1, wherein a volume of the housing at the reference mark is known.

5. The method of claim 4, further comprising determining the infusion rate: by dividing the volume by the time elapsed.

6. The method of claim 1, wherein the housing comprises more than one reference mark.

7. The method of claim 1, wherein the flow controller is configured to receive a tubing configured to receive the fluid.

8. The method of claim 1, further comprising rotating the outer member relative to the housing to align the first aperture with the second aperture and transition the flow controller from the closed position to the open position.

9. A method for calculating an infusion rate in a drip chamber, the method comprising:

providing a housing configured to receive the fluid at a distal end and expel the fluid at a proximal end;

receiving, in the housing, a flow collector that comprises a conical proximal end and a septum extending through the conical proximal end;

applying a force to the flow collector to open the septum and permit the fluid to travel through the septum; and measuring a time elapsed between applying the force and the fluid filling the flow collector.

10. The method of claim 9, wherein a volume of the flow collector is known.

11. The method of claim 10, further comprising determining the infusion rate by dividing the volume by the time elapsed.

12. The method of claim 9, wherein the flow collector has a diameter smaller than a diameter of the housing.

13. The method of claim 9, wherein the housing is configured to receive a tubing configured to receive the fluid.

14. The method of claim 9, wherein the flow collector is coupled to the housing by at least one arm.

15. The method of claim 14, wherein the at least one arm extends from the housing to the flow collector.

16. The method of claim 9, wherein the flow collector is received at a center of the housing.

17. The method of claim 9, wherein the flow collector is fixed relative to the housing.

18. The method of claim 9, wherein the flow collector allows for continuous use of the drip chamber when filled with the fluid.

19. The method of claim 9, wherein the flow collector comprises an open distal end configured to receive the fluid.

20. The method of claim 9, further comprising removing the force from the flow collector to close the septum and prevent the fluid from travelling therethrough.

* * * * *